(12) United States Patent
Alriksson et al.

(10) Patent No.: US 8,871,475 B2
(45) Date of Patent: Oct. 28, 2014

(54) ENZYMATIC HYDROLYSIS OF LIGNOCELLULOSIC MATERIAL IN THE PRESENCE OF SULFITE, DITHIONITE AND/OR DITHIOTHREITOL

(75) Inventors: Bjorn Alriksson, Ornskoldsvik (SE); Leif Jonsson, Umea (SE); Venkata Prabhakar Soudham, Ornskoldsvik (SE)

(73) Assignee: Sekab E-Technology AB (SE)

( * ) Notice: Subject to any disclaimer, the term of this patent is extended or adjusted under 35 U.S.C. 154(b) by 0 days.

(21) Appl. No.: 13/877,837

(22) PCT Filed: Oct. 6, 2010

(86) PCT No.: PCT/SE2010/051080
§ 371 (c)(1),
(2), (4) Date: May 1, 2013

(87) PCT Pub. No.: WO2012/047139
PCT Pub. Date: Apr. 12, 2012

(65) Prior Publication Data
US 2013/0210088 A1    Aug. 15, 2013

(51) Int. Cl.
| | | |
|---|---|---|
| C12P 19/14 | (2006.01) | |
| C12N 1/22 | (2006.01) | |
| C08B 1/00 | (2006.01) | |
| C12P 7/14 | (2006.01) | |
| C12P 19/02 | (2006.01) | |
| C12P 7/16 | (2006.01) | |
| C12P 7/58 | (2006.01) | |
| C12P 7/46 | (2006.01) | |
| C12P 7/40 | (2006.01) | |
| C12P 7/10 | (2006.01) | |

(52) U.S. Cl.
CPC . *C08B 1/003* (2013.01); *C12P 7/14* (2013.01); *C12P 2203/00* (2013.01); *C12P 19/14* (2013.01); *C12P 19/02* (2013.01); *C12P 2201/00* (2013.01); *Y02E 50/10* (2013.01); *C12P 7/16* (2013.01); *C12P 7/58* (2013.01); *C12P 7/46* (2013.01); *C12P 7/40* (2013.01); *Y02E 50/16* (2013.01); *C12P 7/10* (2013.01)

USPC ............ 435/99; 435/145; 435/136; 435/162; 435/160; 127/34

(58) Field of Classification Search
CPC combination set(s) only.
See application file for complete search history.

(56) References Cited

PUBLICATIONS

Sulfite Pretreatment to Overcome Recalcitrance of Lignocellulose (SPORL) for Robust Enzymatic Saccharification of Hardwoods Biotechnol. Prog., 2009, vol. 25, No. 4, p. 1086-1093.*
Aden et al. "Lignocellulosic Biomass to Ethanol Process Design and Economics Utilizing Co-Current Dilute Acid Prehydrolysis and Enzymatic Hydrolysis for Corn Stover, Chapter I.2: Process Overview" National Renewable Energy Laboratory Report pp. 5-6 (Jun. 2002).
Alriksson et al. "Improving the Fermentability of Enzymatic Hydrolysates of Lignocellulose Through Chemical in-situ Detoxification with Reducing Agents" *Bioresource Technology* 102:1254-1263 (2011).
Soudham et al. "Reducing Agents Improve Enzymatic Hydrolysis of Cellulosic Substrates in the Presence of Pretreatment Liquid" *Journal of Biotechnology* 155:244-250 (2011).
Ximenes et al. "Inhibition of Cellulases by Phenols" *Enzyme and Microbial Technology* 46:170-176 (2010).
International Search Report for PCT/SE2010/051080 mailed Oct. 24, 2011, 3 pages.
International Preliminary Report on Patentability for PCT/SE2010/051080, dated Aug. 10, 2012 (13 pages).

* cited by examiner

*Primary Examiner* — Kagnew H Gebreyesus
(74) *Attorney, Agent, or Firm* — Myers Bigel Sibley & Sajovec, P.A.

(57) ABSTRACT

A method is provided for improving enzymatic hydrolysis in saccharification of a lignocellulosic material. The method is comprising pretreating the lignocellulosic material to obtain a slurry of pretreated lignocellulosic material; adding at least one reducing agent to the slurry of pretreated lignocellulosic material or the liquid fraction thereof to decrease the enzymatic hydrolysis inhibitory properties of slurry of the pretreated lignocellulosic material or the liquid fraction thereof; and subjecting the slurry of pretreated lignocellulosic material or the liquid fraction thereof to enzymatic hydrolysis in the presence of the at least one reducing agent.

12 Claims, 2 Drawing Sheets

ENZYMATIC HYDROLYSIS OF LIGNOCELLULOSIC MATERIAL IN THE PRESENCE OF SULFITE, DITHIONITE AND/OR DITHIOTHREITOL

RELATED APPLICATIONS

This application is a 35 U.S.C. §371 national phase application of PCT Application PCT/SE2010/051080, filed Oct. 6, 2010, the entire contents of which are incorporated by reference herein.

TECHNICAL FIELD OF THE INVENTION

The present invention relates to a method for improving enzymatic hydrolysis in saccharification of a pretreated lignocellulosic material. The method provides sugars which are useful as substrates in the manufacture of various target compounds. The method is inter alia useful in the manufacture of a fermentation product, such as ethanol, from the lignocellulosic material.

BACKGROUND TO THE INVENTION

Biorefineries producing commodities from renewable resources offer an alternative to oil refineries based on dwindling supplies of petroleum and permit a move towards improved energy security. Lignocellulosic materials from forestry and agriculture are attractive as feedstocks, since they are abundant, relatively inexpensive, and are not used for food. Lignocellulose consists mainly of lignin and two classes of polysaccharides, cellulose and hemicellulose. The polysaccharides can be hydrolyzed to sugars and converted to various fermentation products, such as bioalcohols, in processes based on biocatalysts, such as the industrially important baker's yeast (*Saccharomyces cerevisiae*).

The hydrolysis of cellulose is typically preceded by a pretreatment, in which the hemicellulose is degraded and the cellulose is made increasingly accessible to cellulolytic enzymes or acidic hydrolysis. Enzymatic hydrolysis of lignocellulosic materials is considered the most promising method to obtain a high yield of glucose from cellulose. By using enzymatic hydrolysis, hydrolysis and fermentation can be performed simultaneously in a simultaneous saccharification and fermentation (SSF) process or in a consolidated bioprocess (CBP). Alternatively, separate hydrolysis and fermentation (SHF) can be used, a process configuration that may also include enzyme-based hydrolysis of the cellulose.

To obtain high yields of sugars from lignocellulosic substrates, dilute acid hydrolysis pretreatment and/or steam pretreatment with acid catalysts are considered appropriate pretreatment methods. Furthermore, in industrial processes for converting lignocellulosic biomass to fermentation products, such as cellulosic ethanol, the whole slurry obtained after pretreatment will probably be used at a high solids concentration. However, the pretreatment liquid is known to inhibit enzymatic hydrolysis.

Previously, addition of surfactants has been considered for improving enzymatic saccharification of cellulosic substrates. Surfactants probably prevent unproductive binding of enzymes to complex lignocellulosic substrates, such as pretreated wood. The economical benefit of adding surfactants to reaction mixtures intended for production of yield-sensitive low-value-added products such as liquid biofuels has, however, been questioned.

The addition of enzymes constitutes a considerable part of the total cost for the process of producing products from lignocellulosic material. The cost for enzymes is for instance regarded as one of the main obstacles for industrial implementation for conversion of lignocellulose to liquid biofuels. It would therefore be desirable to improve the efficiency of the enzymatic hydrolysis of lignocellulosic materials, e.g. to obtain more sugars from a certain enzyme dosage and time period, or to obtain the same amount of sugars from a lower enzyme dosage for the same time period. It is also desirable to achieve a certain amount of sugars with a certain enzyme dosage in a shorter time period, since this increases the production capacity and thereby allows for improved production and/or decreased costs of investment. Improving the efficiency of the enzymatic hydrolysis of cellulose may significantly contribute to commercialization of products based on lignocellulose-derived sugars.

SUMMARY OF THE INVENTION

It is an object of the present invention to improve the efficiency in the process of producing sugars and downstream products from a lignocellulosic material.

It is also an object of the invention to improve the efficiency of the enzymatic hydrolysis in saccharification of lignocellulosic materials.

It is one object of the invention to increase the production capacity in saccharification of lignocellulosic materials.

It is a further object to improve the enzymatic hydrolysis in saccharification of lignocellulosic materials in the presence of pretreatment liquid.

For these and other objects that will be evident to a person skilled in the art from the following disclosure, the present invention provides according to a first aspect a method for improving enzymatic hydrolysis in saccharification of a lignocellulosic material, comprising: pretreating the lignocellulosic material to obtain a slurry of pretreated lignocellulosic material; adding at least one reducing agent to the slurry of pretreated lignocellulosic material or the liquid fraction thereof to decrease the enzymatic hydrolysis inhibitory properties of the slurry of the pretreated lignocellulosic material or the liquid fraction thereof; and subjecting the slurry of pretreated lignocellulosic material or the liquid fraction thereof to enzymatic hydrolysis in the presence of the at least one reducing agent.

In a preferred embodiment, the at least one reducing agent is added to the slurry of pretreated lignocellulosic material; and the slurry of pretreated lignocellulosic material is subjected to enzymatic hydrolysis in the presence of the at least one reducing agent.

In one preferred embodiment, said method is for production of one or more desired target compound(s) from the lignocellulosic material and further comprising the step of utilizing the pretreated and enzymatically hydrolyzed lignocellulosic material as a substrate for production of the target compound(s).

In certain preferred embodiments, the one or more target compound(s) is a fermentation product(s), and the step of utilizing the pretreated and enzymatically hydrolyzed lignocellulosic material is comprising subjecting the pretreated and enzymatically hydrolyzed lignocellulosic material to fermentation. In specific embodiments, the enzymatic hydrolysis step is performed separately from the fermentation step. In other embodiments, the enzymatic hydrolysis and the fermentation are performed simultaneously in a single step. In some embodiments, said fermentation product(s) is including a fermentation product selected from the group consisting of ethanol, butanol and succinic acid, and is preferably ethanol.

In certain other preferred embodiments of the method according to the invention, the target compound is levulinic acid.

In one preferred embodiment, the at least one reducing agent is selected from sulfur oxyanions, sulfhydryl reagents, hydrides and oxidoreductases. In specific embodiments, the at least one reducing agent is selected from sulfite, dithionite and dithiothreitol.

The present invention further provides according to a second aspect a novel use of at least one reducing agent for decreasing the enzymatic hydrolysis inhibitory properties of a slurry of pretreated lignocellulosic material or the liquid fraction thereof.

In a preferred embodiment, said use is for decreasing the enzymatic hydrolysis inhibitory properties of a slurry of pretreated lignocellulosic material.

In one preferred embodiment, the at least one reducing agent is selected from sulfur oxyanions, sulfhydryl reagents, hydrides and oxido-reductases. In specific embodiments, the at least one reducing agent is selected from sulfite, dithionite and dithiothreitol.

DETAILED DESCRIPTION OF THE INVENTION

Figure 1:
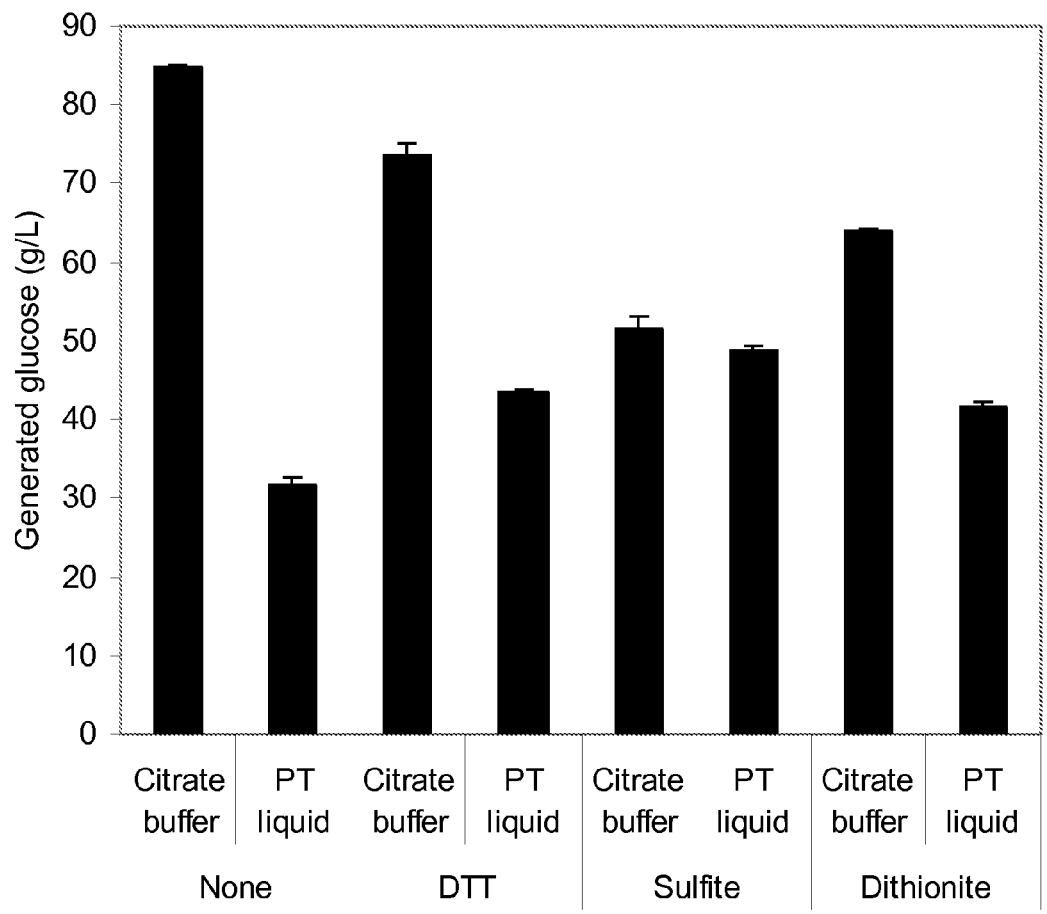
FIG. 1 is a graph showing the effects of addition of different reducing agents (15 mM) on the saccharification of Avicel, a microcrystalline cellulose, after 120 h.

The invention is generally based on the finding that enzymatic hydrolysis of cellulosic substrates in the presence of the liquid fraction obtained after pretreatment of lignocellulose can be enhanced by the addition of reducing agents. This approach differs from the known addition of agents, such as sulfuric acid, sulfur dioxide and sulfite, to the pretreatment to make pretreatment performed at high temperatures more efficient. Addition of these agents in pretreatment utilizes their acidic properties and targets the lignocellulosic substrate and its susceptibility to enzymatic hydrolysis, while addition of reducing agents after pretreatment according to the present invention is contemplated to target enzyme inhibitors in the pretreatment liquid. The present approach also differs from addition of reducing agents to achieve improved fermentability of lignocellulose hydrolysates, since the goal in the latter case is to alleviate the effect of inhibitors on the fermenting microorganism and not, as disclosed herein, on enzymatic hydrolysis.

According to a first aspect, there is provided a method for improving enzymatic hydrolysis in saccharification of a lignocellulosic material. Saccharification refers to conversion or hydrolysis of lignocellulosic material into mono- and disaccharides. The improvement may involve e.g. increasing the cellulose consumption rate, increasing the total amount of sugars produced during the pretreatment and the hydrolysis, increasing the sugar yield on used lignocellulose during pretreatment and hydrolysis, or increasing the volumetric target chemical productivity, e.g. measured as (g target chemical× $L^{-1} \times h^{-1}$). It may also involve maintaining one or more of these parameters using a lower concentration of enzyme or a shorter time period in the hydrolysis step. In the context of the present disclosure, "sugars" refers to fermentable saccharides, such as monosaccharides and disaccharides.

The method is comprising the steps of pretreating the lignocellulosic material to obtain a slurry of pretreated lignocellulosic material; adding at least one reducing agent to the slurry of pretreated lignocellulosic material or the liquid fraction thereof to decrease the enzymatic hydrolysis inhibitory properties of slurry of the pretreated lignocellulosic material or the liquid fraction thereof; and subjecting the slurry of pretreated lignocellulosic material or the liquid fraction thereof to enzymatic hydrolysis in the presence of the at least one reducing agent.

The method according to the invention is directed to treatment of lignocellulosic materials, such as wood chips. The term lignocellulosic materials includes lignocellulose-derived material, i.e. material obtainable from lignocellulosic material, which comprises cellulose, lignin and possibly hemicellulose. The lignocellulose-derived material may for example be derived from wood materials or forestry residues, such as wood chips, sawmill or paper mill discards, or agricultural residues, e.g. corn. As an example, the lignocellulose-derived material may be wood-derived material or sugarcane bagass-derived material. Depending on the geographical location, wood or sugarcane bagass may be available in large quantities, making them attractive as raw materials.

Lignocellulose consists mainly of lignin and two classes of polysaccharides, cellulose and hemicellulose. In saccharification of lignocellulose, the polysaccharides are hydrolyzed to sugars, including disaccharides and monosaccharides. As used herein, hydrolysis refers to subjecting the lignocellulosic material to hydrolyzing conditions such that free sugars becomes accessible in a hydrolysate for further treatment, e.g. fermentation. The free sugars are useful in the manufacture of desired products, such as alcohols, preferably ethanol.

In the method according to the invention, the lignocellulosic material is subjected to a pretreatment, in which the hemicellulose is degraded and the cellulose is made increasingly accessible to cellulolytic enzymes or acidic hydrolysis. Pretreating a lignocellulosic material refers to subjecting the lignocellulosic material to conditions such that the cellulose becomes more accessible during subsequent hydrolysis. The pretreatment may involve one or several pretreatment methods known to the skilled man. As an example, the pretreatment may be performed at elevated temperature with acid, typically dilute mineral acid, such as sulfuric acid, or alkali. The pretreatment may involve impregnation, which refers to impregnating of the cellulosic material with an impregnation fluid, followed by heating. In the case of acid pretreatment, the impregnation fluid may be an acid solution, such as a mineral acid solution. The impregnation may also be performed with a gas, such as a $SO_2$ gas or $CO_2$ gas, or with the combination of a gas with a liquid to obtain e.g. sulfurous acid or carbonic acid. The elevated temperature may be achieved by steaming, a process used to drive air out from the cellulosic biomass to facilitate hydrolysis of the cellulose. Steaming is a well-known method for pretreating e.g. lignocellulosic biomass. As another example, the pretreatment may involve steam explosion, a process that combines steam, rapid pressure releases and hydrolysis for rupturing cellulosic fibers. Depending on the type of pretreatment, it may be desirable to neutralize the pretreated lignocellulosic material prior to the subsequent enzymatic hydrolysis. For example, the pretreated lignocellulosic material may be neutralized by means of a buffer or an addition of NaOH or ammonia. Also, $CaOH_2$ may be used.

A preferred pretreatment involves subjecting the lignocellulosic material to sulfuric acid, sulfurous acid or sulfur dioxide at an elevated temperature, e.g. in the range of 120-220° C., typically for 1-60 min.

The pretreatment provides a slurry of pretreated lignocellulosic material, wherein the hemicellulose is degraded and the cellulose is made increasingly accessible to cellulolytic enzymes or acidic hydrolysis. The suspended solids content of the slurry is typically in the range of from 5 to 40% (w/v), such as from 8 to 30% (w/v), such as from 12 to 20% (w/v). The present invention is based on the observation that the slurry has enzymatic hydrolysis inhibitory properties, and that these inhibitory properties reside in the liquid fraction of the slurry. It is possible to separate the liquid and solid fractions of the slurry obtained after pretreatment of lignocellulosic feedstocks and perform enzymatic hydrolysis in the absence of the liquid fraction. However, it is for practical purposes and for overall process efficiency and economy desirable to utilize the whole slurry of pretreated lignocellulosic material in the subsequent enzymatic hydrolysis process.

Following the pretreatment, the lignocellulosic material is subjected to enzymatic hydrolysis. Enzymatic hydrolysis refers to a hydrolysis reaction catalyzed by at least one enzyme. The at least one enzyme may be at least one saccharification enzyme, which refers to at least one enzyme that can convert or hydrolyze cellulosic biomass into fermentable saccharides, such as monosaccharides and/or disaccharides. Such saccharification enzymes may be glycosidases, which hydrolyze polysaccharides. Examples of glycosidases include cellulose-hydrolyzing glycosidases, such as cellulases, endoglucanases, exoglucanases, cellobiohydrolases and β-glucosidases, hemicellulose hydrolyzing glycosidases, such as xylanases, endoxylanases, exoxylanases, β-xylosidases, arabinoxylanases, mannanases, galactanases, pectinases and glucuronases, and starch hydrolyzing glycosidases, such as amylases, α-amylases, β-amylases, glucoamylases, α-glucosidases and isoamylases, or any enzymes in the group of enzymes found in EC 3.2.1.x, such as EC 3.2.1.4, where EC is the Enzyme Commission number.

In one embodiment, the at least one enzyme originates from filamentous fungi including *Hypocrea jecorina* (*Trichoderma reseei*).

It has now surprisingly been realized that inclusion of reducing agents in the enzymatic hydrolysis makes it possible to obtain a more efficient enzymatic saccharification process in the slurry of pretreated lignocellulosic material, or the liquid fraction thereof. Thus, the enzymatic hydrolysis inhibitory properties of the slurry of the pretreated lignocellulosic material or the liquid fraction thereof can be decreased by addition of at least one reducing agent to the slurry of pretreated lignocellulosic material or the liquid fraction thereof.

In the method according to the invention, the slurry of pretreated lignocellulosic material or the liquid fraction thereof is then subjected to enzymatic hydrolysis in the presence of the at least one reducing agent. This step provides a saccharified lignocellulosic material, e.g. mono- and disaccharides, which can be fermented or otherwise utilized as a substrate for production of desired target compounds.

The liquid fraction can be separated from the slurry of pretreated lignocellulosic material in various ways that are known to the skilled person, e.g. by allowing the solids to settle and decanting the liquid fraction, by centrifugation, by filtration, or combinations of these methods. The suspended solids content of the liquid fraction is typically below 1.0% (w/v), such as below 0.5% (w/v), such as below 0.1% (w/v).

In one embodiment, the at least one reducing agent is added to the liquid fraction of the slurry of pretreated lignocellulosic material. It is noted that while cellulases in general act on solid phase material, cellobiases are active in the liquid phase. Consequently, in one embodiment, the at least one reducing agent is added to the liquid fraction of pretreated lignocellulosic material, and the liquid fraction is then subjected to enzymatic hydrolysis by cellobiases in the presence of the at least one reducing agent.

For practical purposes, it is however convenient to avoid separation procedures and separate treatments for different fractions of the pretreated lignocellulosic material. In a preferred embodiment, the at least one reducing agent is added to the slurry of pretreated lignocellulosic material. The slurry of pretreated lignocellulosic material is then subjected to enzymatic hydrolysis in the presence of the at least one reducing agent.

As shown in the following Examples, the beneficial effects of addition of at least one reducing agent to pretreated lignocellulosic material which is subjected to enzymatic hydrolysis are surprising in at least two ways: Firstly, addition of reducing agents were observed to have a negative effect on enzymatic hydrolysis of cellulose in experiments in which the liquid phase consisted of an aqueous citrate buffer, but a positive effect in a pretreated slurry of lignocellulosic material or in the presence of the liquid portion thereof. Without desiring to be limited to any specific theory, the results suggest that the reducing agents work by protecting the enzymes from compounds present in the pretreatment liquid. Secondly, addition of reducing agent after the pretreatment is beneficial for enzymatic hydrolysis of a slurry of pretreated lignocellulosic material or the liquid fraction thereof regardless of whether sulfur dioxide/sulfite has been used in the pretreatment process.

A "reducing agent" refers to a chemical agent capable of causing the reduction of another substance as it itself is oxidized, i.e. a chemical agent capable of donating an electron in an oxidation-reduction reaction. The reducing agent is compatible with fermenting organisms such as yeast.

In a preferred embodiment, the at least one reducing agent is selected from sulfur oxyanions, sulfhydryl reagents, hydrides and oxidoreductases. In one preferred embodiment, the at least one reducing agent comprises sulfur. As an example, the at least one reducing agent may be selected from dithionite, sulfite and dithiothreitol. These reducing agents have shown to be suitable for decreasing the inhibition of enzymatic hydrolysis as shown in the Examples of the present disclosure. Dithionite and sulfite (hydrogen sulfite at the pH used for enzymatic saccharification) are sulfur oxyanions. Sulfite ($SO_3^{2-}$), derived from sulfur dioxide gas or from addition of salt, is used in several large-scale industrial processes, including pretreatment of lignocellulosic substrates. Dithionite ($S_2O_4^{2-}$) is an industrial chemical used in the pulp and paper industry for reductive bleaching and in the textile industry as a reducing agent in dyeing processes. Hence, both sulfite and dithionite are available in large quantities. Further, it is to be understood the reducing agent may comprise sulfite and/or dithionite in salt form, i.e. complexed with different cations. Examples include $Na_2SO_3$, $NaHSO_3$, $KHSO_3$, and $Na_2S_2O_4$. Dithiothreitol (DTT), also known as Cleland's reagent, represents sulfhydryl compounds. DTT is interesting in this context considering that it is known to efficiently reduce disulfide bonds in proteins. Reducing agents like DTT could therefore tentatively have a detrimental effect by destabilizing proteins with disulfide bridges.

As an example, the reducing agent may be dithionite, and the dithionite may be added in an amount such that the concentration of dithionite during enzymatic hydrolysis is above 1 mM, such as above 5 mM, or in the range of 1-30 mM, such as 5-25 mM, such as 7.5-20 mM. As a further example, the reducing agent is sulfite, and the sulfite is added in an amount such that the concentration of sulfite during enzymatic hydrolysis is above 1 mM, such as above 5 mM, or in the range of 1-30 mM, such as 5-25 mM, such as 7.5-20 mM. As yet another example, the reducing agent is dithiothreitol, and the dithiothreitol is added in an amount such that the concentration of dithiothreitol during enzymatic hydrolysis is above 1 mM, such as above 5 mM, or in the range of 1-30 mM, such as 5-25 mM, such as 7.5-20 mM.

These concentrations of dithionite, sulfite and dithiothreitol, respectively, have shown to be suitable for decreasing inhibition of enzymatic hydrolysis, as shown in the Examples of the present disclosure. It may however be disadvantageous for a subsequent fermentation process to add more than 100 mM of sulfite. Thus, the amounts of reducing agent required to achieve a decrease in enzymatic hydrolysis inhibitory properties are relatively low and the results from Examples of the present disclosure indicate that such amounts of reducing agent permit production of high levels of sugars.

Other compounds that may be used as reducing agents include thiosulfates ($S_2O_3^{2-}$), such as $Na_2S_2O_3.5H_2O$ and $Na_2S_2O_3$, alkali-decomposed sugars, ascorbic acid, cysteine, diethanolamine, triethanolamine, and reduced glutathione.

Sulfur oxyanions, such as sulfite and dithionite, can also efficiently improve the fermentability of lignocellulose hydrolysates to levels that give similar yields of fermentation product as are obtained with reference fermentations based on synthetic sugar solutions. The usefulness of sulfur oxyanions for improving pretreatment and fermentability makes the approach to enhance the efficiency of enzymatic hydrolysis presented herein even more attractive from an industrial perspective, since the same chemical can be used for different purposes in different parts of the process.

As set out above, the present method provides a saccharified lignocellulosic material, e.g. mono- and disaccharides, which can be fermented or otherwise utilized as a substrate for production of desired target compounds. These sugars can be utilized as substrates in various chemical and biochemical (e.g. enzymatic) methods for production of desired target compounds. By way of example, the sugars can be used in a thermochemical process to produce levulinic acid, which in turn is an intermediate in the synthesis of polymers, plastics and pharmaceuticals. It is also a precursor in the industrial production of other chemical commodities such as methyltetrahydrofuran, valerolactone, and ethyl levulinate. According to one embodiment, said method further involves the step of utilizing the pretreated and enzymatically hydrolyzed lignocellulosic material as a substrate for production of target compounds. If the liquid fraction has been separated from the slurry of pretreated lignocellulosic material prior to the enzymatic hydrolysis, the further use of the pretreated and enzymatically hydrolyzed lignocellulosic material as a substrate for production of target compounds may be performed with the liquid fraction alone. Alternatively, the liquid fraction may be combined with the original slurry from which it is derived, which slurry has also been subjected to enzymatic hydrolysis, and then be subjected to the further use.

The present method also offers a way to achieve more efficient saccharification of lignocellulose in the manufacture of fermentation products from lignocellulose hydrolysates. Examples of fermentation products according to the invention include alcohols, acids, alkanes, alkenes, aromatics, aldehydes, ketones, biopolymers, proteins, peptides, amino acids, vitamins, antibiotics and other pharmaceuticals. In one embodiment, the fermentation product is selected from the group consisting of ethanol, butanol and succinic acid. A preferred fermentation product is ethanol. Consequently, the method according to the invention also provides for an efficient production of fuels, such as ethanol, and other chemicals from lignocellulosic materials. According to one embodiment, said method is for improving saccharification of lignocellulose in production of a fermentation product from lignocellulosic material and further involves the step of subjecting the pretreated and enzymatically hydrolyzed lignocellulosic material to fermentation.

If the liquid fraction has been separated from the slurry of pretreated lignocellulosic material prior to the enzymatic hydrolysis, the further fermentation of the pretreated and enzymatically hydrolyzed lignocellulosic material may be performed with the liquid fraction alone. Optionally, the fermented liquid fraction may then be returned to the to the original slurry and facilitate liberation of monosaccharides from the solids in the slurry. Alternatively, the liquid fraction may be combined with the original slurry, which has also been subjected to enzymatic hydrolysis, and then be subjected to fermentation.

The fermentation of the pretreated and enzymatically hydrolyzed lignocellulosic material may be performed by a fermenting organism, which refers to an organism that is capable of fermenting sugars, e.g. mono- or disaccharides into a fermentation product. The fermenting organism may be at least one eukaryotic or prokaryotic microorganism, such as bacteria and/or yeast. Examples of bacteria and yeasts which are capable of fermenting saccharides into other chemical compounds are known to the skilled person. Yeasts from *Saccharomyces, Pichia* and *Candida* may be used as the fermenting organism. The fermenting organism may for example be wild type, mutant or recombinant *Saccharomyces cerevisiae*. Using *S. cerevisiae* for producing a fermentation product is advantageous since *S. cerevisiae* is well established with regard to industrial fermentation and provides for a high product yield.

In one embodiment, the fermentation is a simultaneous saccharification and fermentation (SSF) of a pretreated lignocellulosic material. A SSF process refers to a process in which enzymatic hydrolysis and fermentation is performed simultaneously in a fermentor. Thus, in a SSF process, fermentable saccharides are prepared directly in a fermentor by enzymatic hydrolysis of the pretreated lignocellulosic material, and the resulting saccharides are converted into a fermentation product. Further, the fermentation may be a consolidated bioprocess (CBP), in which the biocatalyst that convert the monosaccharides also produces the enzymes that hydrolyze the pretreated lignocellulosic material.

In another embodiment, the hydrolysate that is subjected to fermentation is obtained from enzymatic hydrolysis of the pretreated lignocellulosic material in a step separate from the fermentation step. Consequently, the enzymatic hydrolysis and the fermentation may be performed as two separate process steps (separate hydrolysis and fermentation, SHF). This may e.g. be advantageous if the fermentation reaction and the enzymatic reaction have different optimal temperatures. As an example, the temperature during enzymatic hydrolysis may be kept higher than the temperature during fermentation, thus facilitating the use of thermophilic enzymes. While the enzymatic hydrolysis is generally performed prior to the fermentation step, it is noted that the fermented material or parts thereof, e.g. a liquid fraction, may be returned to the to the original slurry and facilitate liberation of monosaccharides from the solids in the slurry, which may then be subjected to fermentation.

According to a second aspect, there is provided a novel use of at least one reducing agent for decreasing the enzymatic hydrolysis inhibitory properties of a slurry of pretreated lignocellulosic material or the liquid fraction thereof. In a preferred embodiment, the at least one reducing agent is useful specifically for decreasing the enzymatic hydrolysis inhibitory properties of a slurry of pretreated lignocellulosic material.

As set out above, the at least one reducing agent is preferably selected from sulfur oxyanions, sulfhydryl reagents, hydrides and oxidoreductases, such as sulfite, dithionite and dithiothreitol.

The following non-limiting examples will further illustrate the present invention.

EXAMPLES

Example 1

Pretreatment of Lignocellulosic Material from Spruce

Pretreatment of unbarked wood chips of Norway spruce (*Picea abies*) was performed by treatment in a continuous mode with sulfur dioxide at a temperature of 203° C. for 5 min in a 30 liters reactor. One kg of sulfur dioxide was used per 40 kg of wood chips. After the pretreatment, the pH of the slurry was 2 and the dry matter content was 16%. The slurry of pretreated material was cooled to room temperature and stored at 4° C. until further use. Before inclusion in reaction mixtures, the pH of the slurry was adjusted to 5.2 using a 5 M solution of NaOH, and the slurry was diluted with water to achieve the desired concentration of cellulosic substrate.

The liquid fraction of the pretreated spruce, hereafter referred to as the pretreatment liquid, was obtained by filtration. The concentrations of monosaccharides, acetic acid, and furan aldehydes in the pretreatment liquid were: 22.7 g/l mannose, 18.4 g/l glucose, 11.3 g/l xylose, 5.6 g/l galactose, 3.6 g/l arabinose, 5.6 g/l acetic acid, 3.6 g/l 5-hydroxymethylfurfural (HMF), and 2.1 g/l furfural. Before inclusion in reaction mixtures, the pH of the pretreatment liquid was adjusted to 5.2 using a 5 M solution of NaOH.

Filter cake of pretreated spruce wood was obtained by filtration of the slurry and washing of the solid fraction with 4-5 volumes of distilled water. The resulting filter cake was then dried over night in an oven at 70° C., milled by using an IKA A 11 basic analytical mill (IKA, Staufen, Germany) and stored at room temperature until used. The dry matter content of the filter cake was analyzed using a moisture analyzer (MJ 33, Mettler Toledo, Switzerland).

Example 2

Enzymatic Saccharification of Microcrystalline Cellulose

Hydrolysis experiments were conducted in 100 ml E-flasks, equipped with cotton plugs and containing reaction mixtures with a total mass of 25 g. The mixtures contained a reaction medium, either pretreatment liquid from Example 1 or a 0.05 M citrate buffer solution, pH 5.2; 10% (w/w) microcrystalline cellulose Avicel PH 101 (Fluka, Buchs, Switzerland); and 2% (w/w) enzyme cocktail consisting of equal amounts of Celluclast 1.5 L and Novozyme 188 (both from Sigma-Aldrich, St. Louis, Mo., USA). The stated activities of the enzyme preparations were: Celluclast 1.5 L, 700 endoglucanase units (EGU)/g; Novozyme 188, 250 cellobiase units (CBU)/g. Some mixtures also contained one of the following reducing agents (all of reagent grade): sodium dithionite ($Na_2S_2O_4$) (Merck, Darmstadt, Germany), sodium sulfite ($Na_2SO_3$) (Merck), and dithiothreitol (DTT) (Sigma-Aldrich), which were added to a final concentration of 15 mM.

The E-flasks were incubated for 120 h at 45° C. in an orbital shaker (Ecotron incubator shaker, Infors, Bottmingen, Switzerland) set at 170 rpm. During the hydrolysis, 100 µl samples were collected after 0, 6, 12, 18, 24, 36, 48, 72, 96, and 120 h. In the beginning and after completion of the hydrolysis (i.e. at 0 and 120 h), 1.5 ml samples were also taken.

Samples were chilled on ice, and centrifuged at 14 100 g for 5 min. The supernatants were collected and their glucose concentration was analyzed using a glucometer (Glucometer Elite XL, Bayer AG, Leverkusen, Germany). Analyses of the sugar content of selected samples were also performed using ion chromatography (IC) and high performance liquid chromatography (HPLC). The glucometer values, which have satisfactory precision but low accuracy, were corrected using data obtained by chromatographic determination of glucose. The effects of different reducing agents on the enzymatic saccharification of Avicel are presented in Table 1 and FIG. 1. FIG. 1 presents the effects of different reducing agents (15 mM) on the saccharification of Avicel after 120 h, wherein PT liquid denotes pretreatment liquid, and the error bars indicate the standard deviations.

TABLE 1

Effects of different reducing agents on the saccharification of Avicel

| Reducing agent added[a] | Medium | Glucose concentration[c] (g/l) | | | | | | | | |
|---|---|---|---|---|---|---|---|---|---|---|
| | | After 6 h | After 12 h | After 18 h | After 24 h | After 36 h | After 48 h | After 76 h | After 96 h | After 120 h |
| DTT | Citrate buffer | 23.1 (0.2) | 29.9 (0.2) | 33.9 (<0.1) | 35.4 (<0.1) | 39.8 (0.8) | 44.1 (0.5) | 52.6 (0.2) | 63.1 (0.8) | 73.4 (1.6) |
| | PT liquid[b] | 9.2 (0.4) | 12.1 (0.2) | 16.3 (0.8) | 18.4 (0.8) | 19.6 (0.2) | 23.1 (0.2) | 30.1 (1.0) | 40.0 (1.2) | 43.3 (0.5) |
| Sulfite | Citrate buffer | 10.7 (0.2) | 15.2 (0.2) | 20.9 (0.2) | 23.0 (0.6) | 25.8 (0.2) | 31.5 (0.2) | 40.2 (0.6) | 44.8 (1.6) | 51.6 (1.6) |
| | PT liquid[b] | 8.9 (<0.1) | 14.5 (0.8) | 18.5 (0.2) | 19.3 (0.2) | 21.6 (0.2) | 26.1 (0.2) | 33.3 (0.2) | 42.1 (0.8) | 48.7 (0.5) |
| Dithionite | Citrate buffer | 13.9 (0.2) | 19.2 (0.2) | 26.7 (0.5) | 28.6 (0.8) | 31.9 (0.8) | 36.1 (1.2) | 45.8 (1.1) | 54.8 (1.2) | 63.9 (0.4) |
| | PT liquid[b] | 10.5 (0.2) | 17.0 (0.2) | 20.9 (0.5) | 22.0 (<0.1) | 23.8 (0.4) | 27.5 (0.8) | 33.0 (<0.1) | 39.6 (1.4) | 41.6 (0.7) |
| None | Citrate buffer | 20.5 (0.5) | 29.9 (0.2) | 36.7 (0.5) | 40.0 (0.2) | 45.1 (0.5) | 53.0 (0.2) | 60.0 (1.2) | 75.4 (0.4) | 84.8 (<0.1) |
| | PT | 8.6 | 14.4 | 16.4 | 17.7 | 19.9 | 21.8 | 25.3 | 27.4 | 31.7 |

TABLE 1-continued

Effects of different reducing agents on the saccharification of Avicel

| Reducing agent added[a] | Medium | Glucose concentration[c] (g/l) | | | | | | | | |
|---|---|---|---|---|---|---|---|---|---|---|
| | | After 6 h | After 12 h | After 18 h | After 24 h | After 36 h | After 48 h | After 76 h | After 96 h | After 120 h |
| | liquid[b] | (0.2) | (1.0) | (0.6) | (<0.1) | (0.2) | (0.8) | (<0.1) | (1.2) | (0.8) |

[a]Avicel was hydrolyzed in the presence or absence of 15 mM of the reducing agents.
[b]PT liquid = pretreatment liquid
[c]Glucose production calculated as the average of duplicate experiments for each reaction. The table shows the glucose generated during the experiment, with the initial glucose content of the pretreatment liquid deducted. Standard deviations are shown within parentheses.

Reducing agents could tentatively have a detrimental effect by destabilizing proteins with disulfide bridges. Indeed, all three reducing agents studied had a negative effect on enzymatic hydrolysis of cellulose in experiments in which the liquid phase consisted of an aqueous citrate buffer. After 120 h, the generation of glucose from Avicel was 13-39% lower in the presence of 15 mM of reducing agent than in control reactions without reducing agent. Sulfite had the most detrimental effect, followed by dithionite, and then DTT.

In the presence of pretreatment liquid from spruce wood, inclusion of reducing agents surprisingly had a positive effect on the hydrolysis of cellulose. Addition of 15 mM of reducing agent resulted in 31-54% higher production of glucose from Avicel after 120 h. Sulfite gave the highest glucose concentration, followed by DTT, and then dithionite. The improvement achieved with the different reducing agents was not inversely related to the negative impact on enzymatic hydrolysis in the citrate buffer system. Despite the fact that sulfite had the largest negative impact, it gave the highest final glucose concentration (Table 1, FIG. 1). The negative effects of changing from a citrate buffer regime to a pretreatment liquid regime ranged from 63% decrease in glucose production after 120 h for the control without reducing agent, to 41% for DTT, 35% for dithionite, and 6% for sulfite.

Example 3

Enzymatic Saccharification of Pretreated Spruce Slurry

Hydrolysis experiments were conducted in 100 ml E-flasks, equipped with cotton plugs and containing reaction mixtures with a total mass of 25 g. The mixtures contained a pretreated spruce slurry from Example 1 adjusted to 10% (w/w) solids, pH 5.2; and 0.5, 1, 2 or 4% (w/w) enzyme cocktail consisting of equal amounts of Celluclast 1.5 L and Novozyme 188. The enzymatic hydrolysis was carried out in the presence or absence of 15 mM dithionite.

The E-flasks were incubated for 120 h at 45° C. in an orbital shaker set at 170 rpm. During the hydrolysis, 100 μl samples were collected after 6, 24, 48, 76, 96, and 120 h. In the beginning and after completion of the hydrolysis (i.e. at 0 and 120 h), 1.5 ml samples were also taken.

Figure 2:
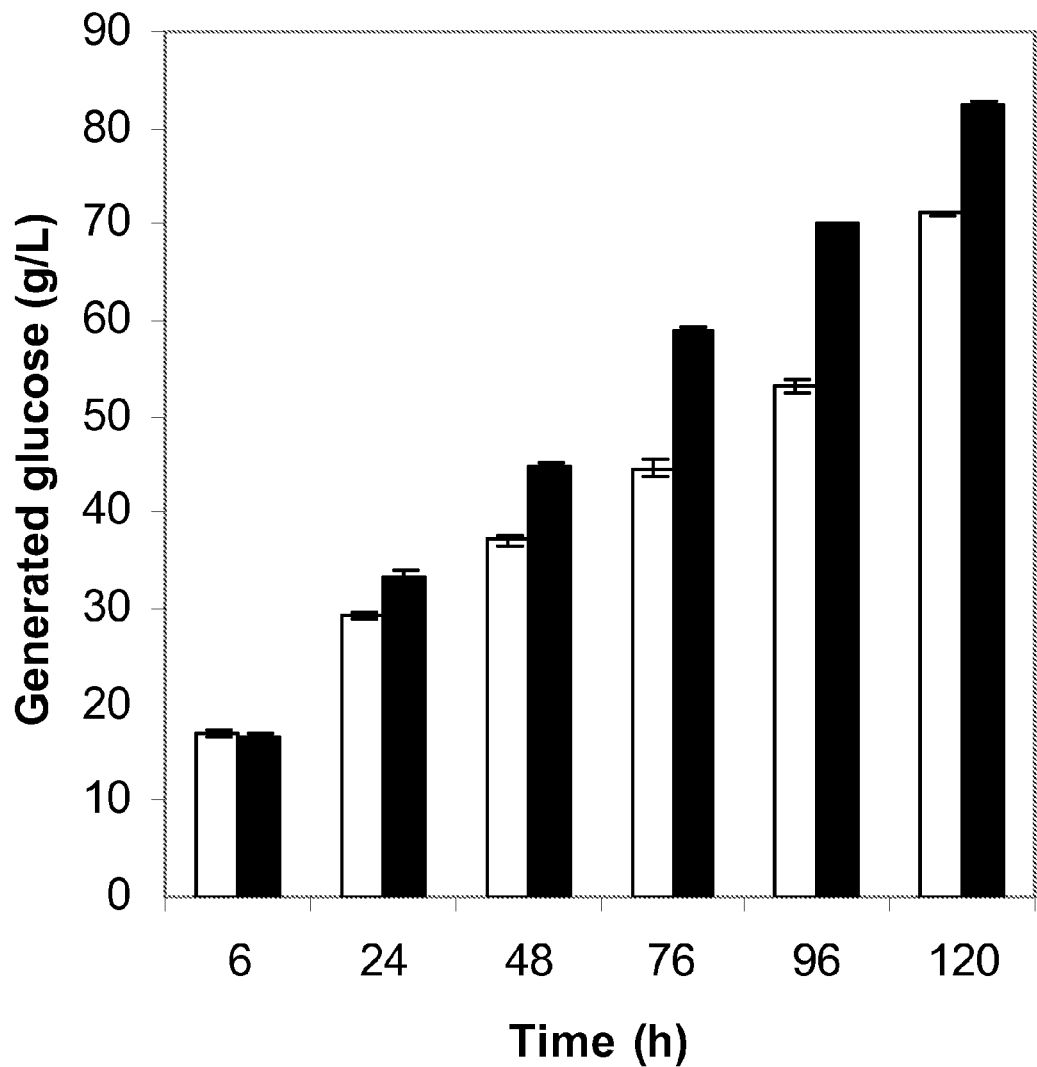
FIG. 2 is a graph showing the effects of addition of 15 mM dithionite on the saccharification of a pretreated spruce slurry.

Samples were chilled on ice, and centrifuged at 14 100 g for 5 min. The supernatants were collected and their glucose concentration was analyzed using a glucometer. Analyses of the sugar content of selected samples were also performed using IC and HPLC. The glucometer values were corrected using data obtained by chromatographic determination of glucose. The effects of the reducing agent dithionite on the saccharification of pretreated spruce slurry for various enzyme loadings are presented in Table 2 and FIG. 2. In FIG. 2, the effects of addition of 15 mM dithionite (black bars) on saccharification of a pretreated spruce slurry with 4% enzyme loading is shown, compared to no addition of reducing agent (white bars). Error bars indicate the standard deviations

TABLE 2

Saccharification of pretreated spruce slurry with different enzyme loading

| Enzyme loading % (w/w) | Reducing agent added[a] | Glucose concentration[b] (g/l) | | | | | |
|---|---|---|---|---|---|---|---|
| | | After 6 h | After 24 h | After 48 h | After 76 h | After 96 h | After 120 h |
| 4 | Dithionite | 16.7 | 33.4 | 44.7 | 58.9 | 70.1 | 82.5 |
| | | (0.2) | (0.5) | (0.2) | (0.2) | (0.2) | (0.2) |
| | None | 17.1 | 29.2 | 37.1 | 44.6 | 53.1 | 71.1 |
| | | (0.4) | (0.4) | (0.5) | (0.8) | (0.6) | (0.2) |
| 2 | Dithionite | 11.4 | 22.4 | 31.2 | 40.7 | 49.0 | 57.5 |
| | | (0.5) | (0.8) | (0.4) | (0.2) | (1.4) | (0.9) |
| | None | 11.9 | 20.4 | 27.9 | 36.6 | 42.0 | 51.0 |
| | | (0.2) | (0.2) | (0.2) | (0.6) | (0.4) | (1.0) |
| 1 | Dithionite | 6.2 | 15.4 | 23.1 | 29.9 | 36.7 | 45.8 |
| | | (0.2) | (0.2) | (0.2) | (0.2) | (2.2) | (1.1) |
| | None | 5.2 | 13.5 | 19.6 | 25.7 | 31.3 | 40.0 |
| | | (0.5) | (0.2) | (0.6) | (1.0) | (0.5) | (2.2) |
| 0.5 | Dithionite | 4.1 | 10.4 | 17.1 | 23.0 | 27.9 | 35.0 |
| | | (<0.1) | (0.6) | (0.4) | (0.4) | (0.9) | (2.3) |
| | None | 3.4 | 8.9 | 14.5 | 20.2 | 23.9 | 30.1 |
| | | (0.8) | (0.8) | (0.8) | (2.1) | (2.3) | (2.8) |

[a]Slurry of pretreated spruce wood was hydrolyzed in the presence or absence of 15 mM dithionite.
[b]Glucose production calculated as the average of duplicate experiments. The table shows the glucose generated during the experiment, with the initial glucose content of the pretreatment liquid deducted. Standard deviations are shown within parentheses.

Regardless of the enzyme loading, inclusion of dithionite always resulted in higher final glucose yield. The improvement compared to reactions without any added reducing agent amounted to 13-16% after 120 h. These values are lower than the positive effect of dithionite on Avicel (Example 2, Table 1), which was 31% after 120 h. However, since the slurry was diluted with water to achieve 10% concentration of cellulosic substrate, the reaction mixture with slurry contained less pretreatment liquid than comparable reactions with Avicel. Furthermore, after 76 and 96 h, the improvement with dithionite reached 32% in the experiment with 4% enzyme loading (Table 2, FIG. 2). Higher enzyme loading gave higher glucose concentrations, but the experiment shows that if a reducing agent is added after pretreatment, it is possible to reduce the enzyme loading and still obtain a similar sugar yield.

The pretreatment process of Example 1, designed to improve the enzymatic digestibility of softwood, was performed at a high temperature (>200° C.) with addition of sulfur dioxide, which forms sulfite in an aqueous solution. The fact that addition of dithionite after pretreatment resulted in improved enzymatic hydrolysis at only 45° C. indicates that addition of reducing agent after the pretreatment is beneficial for enzymatic hydrolysis, even if sulfur dioxide/sulfite has been used in the pretreatment process.

Example 4

Enzymatic Saccharification of Filter Cake from Pretreated Spruce

Hydrolysis experiments were conducted in 100 ml E-flasks, equipped with cotton plugs and containing reaction mixtures with a total mass of 25 g. The mixtures contained as a reaction medium either pretreatment liquid from Example 1 or a 0.05 M citrate buffer solution, pH 5.2; 10% (w/w) filter cake of pretreated spruce wood as cellulosic substrate; and 2% (w/w) enzyme cocktail consisting of equal amounts of Celluclast 1.5 L and Novozyme 188. The enzymatic hydrolysis was carried out in the presence or absence of 15 mM dithionite.

The E-flasks were incubated for 120 h at 45° C. in an orbital shaker set at 170 rpm. During the hydrolysis, 100 µl samples were collected after 6, 12, 24, 36, 48, 76, 96, and 120 h. In the beginning and after completion of the hydrolysis (i.e. at 0 and 120 h), 1.5 ml samples were also taken.

Samples were chilled on ice, and centrifuged at 14 100 g for 5 min. The supernatants were collected and their glucose concentration was analyzed using a glucometer. Analyses of the sugar content of selected samples were also performed using IC and HPLC. The glucometer values were corrected using data obtained by chromatographic determination of glucose. The effects of the reducing agent dithionite on the enzymatic saccharification of pretreated spruce wood are presented in Table 3.

TABLE 3

Enzymatic saccharification of filter cake of pretreated spruce wood

| Medium | Reducing agent added[a] | Glucose concentration[b] (g/l) | | | | | | | |
|---|---|---|---|---|---|---|---|---|---|
| | | After 6 h | After 12 h | After 24 h | After 36 h | After 48 h | After 76 h | After 96 h | After 120 h |
| Citrate buffer | Dithionite | 8.6 (0.2) | 12.3 (0.2) | 16.3 (0.4) | 19.7 (0.4) | 21.8 (0.4) | 24.3 (0.2) | 27.4 (0.5) | 31.0 (0.6) |
| | None | 9.9 (0.2) | 12.8 (0.5) | 16.3 (0.6) | 19.2 (0.2) | 20.9 (0.6) | 23.1 (0.5) | 25.7 (0.5) | 29.0 (0.2) |
| PT liquid[c] | Dithionite | 6.4 (0.2) | 10.2 (0.4) | 11.8 (<0.1) | 15.5 (0.2) | 16.8 (0.2) | 18.2 (0.6) | 21.1 (0.4) | 24.7 (1.1) |
| | None | 5.4 (0.2) | 6.4 (0.2) | 7.9 (0.5) | 11.3 (0.4) | 12.5 (0.2) | 13.5 (0.6) | 15.4 (0.2) | 18.6 (<0.1) |

[a]Spruce wood filter cake was hydrolyzed in the presence or absence of 15 mM dithionite.
[b]Glucose production calculated as the average of duplicate experiments. The table shows the glucose generated during the experiment, with the initial glucose content of the pretreatment liquid deducted. Standard deviations are shown within parentheses.
[c]PT liquid = pretreatment liquid The glucose production from the washed and milled filter cake was improved by 7% after 120 h by addition of dithionite to reaction mixtures with citrate buffer. That is different from the experiment with microcrystalline cellulose (Avicel, Example 2, Table 1), where addition of dithionite to a citrate buffer regime resulted in decreased glucose production. The presence of the lignocellulosic material in the washed and milled filter cake seemed to alleviate the negative effects of the reducing agent on the enzymatic hydrolysis in the absence of pretreatment liquid. The pretreatment process would degrade the hemicellulose in the spruce wood, which is also evident from the formation of mannose, xylose, and other hemicellulose-derived compounds in the pretreatment liquid. However, most of the lignin would be left in the solid fraction together with the cellulose, and probably also some lipophilic extractives. Furthermore, despite that the filter cake was washed with water, there may be some low-molecular mass compounds generated in the pretreatment process that nevertheless stick to the solid fraction by hydrophobic interactions. The chemical composition of the material in the filter cake is thus quite different from that of Avicel, which simply consists of microcrystalline cellulose. This difference in chemical composition may explain the different effects observed for dithionite in citrate buffer regimes.

In the presence of pretreatment liquid, the improvement in glucose production that resulted from inclusion of dithionite reached 33% after 120 h. That improvement was similar to the improvements caused by dithionite in the experiments with microcrystalline cellulose (Avicel) in pretreatment liquid (Example 2, Table 1).

The invention claimed is:

1. A method for improving enzymatic hydrolysis in saccharification of a lignocellulosic material, comprising:
    pretreating the lignocellulosic material with an acid or $SO_2$ to obtain a slurry of pretreated lignocellulosic material;
    adding at least one reducing agent, wherein the at least one reducing agent is selected from sulfur oxyanions and sulfhydryl reagents, to the slurry of pretreated lignocellulosic material or the liquid fraction thereof to decrease the enzymatic hydrolysis inhibitory properties of the slurry of the pretreated lignocellulosic material or the liquid fraction thereof; and
    subjecting the slurry of pretreated lignocellulosic material or the liquid fraction thereof to enzymatic hydrolysis in the presence of the at least one reducing agent.

2. A method according to claim 1, wherein the at least one reducing agent is added to the slurry of pretreated lignocellulosic material; and the slurry of pretreated lignocellulosic material is subjected to enzymatic hydrolysis in the presence of the at least one reducing agent.

3. A method according to claim 1, wherein said method is for production of one or more desired target compound(s) from the lignocellulosic material and further comprising the step of
    utilizing the pretreated and enzymatically hydrolyzed lignocellulosic material as a substrate for production of the target compound(s).

4. A method according to claim 3, wherein the one or more target compound(s) is a fermentation product(s), and the step of utilizing the pretreated and enzymatically hydrolyzed lignocellulosic material comprises subjecting the pretreated and enzymatically hydrolyzed lignocellulosic material to fermentation.

5. A method according to claim 4, wherein the enzymatic hydrolysis step is performed separately from the fermentation step.

6. A method according to claim 4, wherein the enzymatic hydrolysis and the fermentation are performed simultaneously in a single step.

7. A method according to claim 4, wherein said fermentation product(s) includes a fermentation product selected from the group consisting of ethanol, butanol and succinic acid.

8. A method according to claim 7, wherein said fermentation product is ethanol.

9. A method according to claim 3, wherein the target compound is levulinic acid.

10. A method according to claim 1, wherein the at least one reducing agent is selected from the group consisting of sulfite, dithionite and dithiothreitol.

11. A method for decreasing the enzymatic hydrolysis inhibitory properties of a slurry of lignocellulosic material pretreated with an acid or $SO_2$ or the liquid fraction thereof, said method comprising the use of at least one reducing agent selected from the group consisting of sulfur oxyanions and sulfhydryl reagents.

12. The method according to claim 11, wherein the at least one reducing agent is selected from sulfite, dithionite and dithiothreitol.

\* \* \* \* \*